United States Patent [19]

Ko

[11] Patent Number: 5,354,302
[45] Date of Patent: Oct. 11, 1994

[54] MEDICAL DEVICE AND METHOD FOR FACILITATING INTRA-TISSUE VISUAL OBSERVATION AND MANIPULATION OF DISTENSIBLE TISSUES

[76] Inventor: Sung-Tao Ko, 42 Baybrook La., Oak Brook, Ill. 60521

[21] Appl. No.: 973,082

[22] Filed: Nov. 6, 1992

[51] Int. Cl.⁵ .......................... A61F 2/32; A61F 2/34; A61B 17/58; A61B 17/60
[52] U.S. Cl. .................................. 606/104; 604/161; 128/4
[58] Field of Search ...................... 606/13, 14, 17, 198; 604/104-109, 118, 119, 161, 171; 128/3-11, 20, 22

[56] References Cited

U.S. PATENT DOCUMENTS

| | | |
|---|---|---|
| 3,517,128 | 6/1970 | Hines . |
| 3,980,078 | 9/1976 | Tominaga .................. 128/4 |
| 4,023,559 | 5/1977 | Gaskell . |
| 4,043,323 | 8/1977 | Komiya ..................... 128/4 |
| 4,281,646 | 8/1981 | Kinoshita ................... 128/6 |
| 4,607,619 | 8/1986 | Seike et al. ................. 128/4 |
| 4,773,394 | 9/1988 | Reichstein et al. ........... 128/et al. |
| 5,178,133 | 1/1993 | Pena ....................... 128/20 |
| 5,197,971 | 3/1993 | Bonutti . |
| 5,203,773 | 4/1993 | Green ...................... 604/104 |

OTHER PUBLICATIONS

Karl Storz *Resectoscope Catalog*, Germany, believed to be published in 1988. pp. RES 1-RES 18A.
Richard Wolf *Laparoscopy And Hysteroscopy Catalog*, available from Richard Wolf Medical Instrument Corp. 7046 Lyndon Avenue, Rosemont, Illinois 60018, U.S.A., believed to be printed in 1989. See particularly pp. E1-E52.

*Primary Examiner*—C. Fred Rosenbaum
*Assistant Examiner*—V. Alexander
*Attorney, Agent, or Firm*—Welsh & Katz, Ltd.

[57] ABSTRACT

A device for facilitating intra-tissue observation and/or manipulation includes an outer sleeve having a first end and a second end and an inner sheath member adapted for insertion into the second end, wherein the first end is a penetration end adapted to move tissue away from the penetration end. A preferred embodiment of the penetration end includes a hollow cone adapted to expand and retract upon axial movement of the inner sheath such that expansion of the penetration end moves tissue away from the first end to form an open operating area. The inner sheath member includes a scope, such as an optically based telescope, for visually observing an area proximate the first end. A pronged grip device secures the outer sleeve about the opening. The pronged grip device includes adjustable prongs which are axially slidable along the outer sleeve and radially contractible to substantially form an airtight seal between the outer sleeve and the opening. A method for using the device includes inserting the device into the opening; adjusting the prong device about the opening so as to substantially form an airtight seal between the outer sleeve and the opening; and moving the inner member and the outer member relative to each other to engage the penetration end so move tissue away from the end to provide an open working area and injecting gas into the open area to further distend the tissue.

19 Claims, 4 Drawing Sheets

MEDICAL DEVICE AND METHOD FOR FACILITATING INTRA-TISSUE VISUAL OBSERVATION AND MANIPULATION OF DISTENSIBLE TISSUES

BACKGROUND OF THE INVENTION

The invention relates generally to medical devices for facilitating visual observation and manipulation of internal tissue and more particularly to devices for facilitating direct intra-tissue visual observation and manipulation of solid distensible tissues, such as muscle tissue, tumors, solid organs, tissue between tissue planes such as preperitoneal tissue, or similar tissue configurations.

Oftentimes, solid tissue formations such as muscle tissue, fatty tissue or tumors, must be operated on or examined to determine whether there is an anomaly within the tissue. There exists a need for a medical instrument which allows an operator to visually inspect and/or operate within the tissue without requiring a large incision in the body to examine or perform operations on the organ or tissue. For example, where the tissue or organ of interest is not a viscus or does not have a cavity within the organ, it is difficult to get a visual image using known devices. Consequently, there exists a need for a medical instrument suitable for intra-tissue dissections and/or for intra-tissue suturing while visually monitoring the area of dissection.

Known intra-cavitary endoscopes, e.g., laparoscopes, pelviscopes, gastroscopes, colonoscopes, etc., are typically designed to facilitate visual examination and manipulation of body cavities, the exterior of viscera and lumen of a viscera. However, no medical instruments are known which facilitate visual observation and simultaneous manipulation or dissecting operations within a relatively solid organ or tissue.

Laparoscopes, for example, find particular use in abdominal surgery. These devices typically include a tubular member which has internal channels for housing various operating instruments. One channel typically houses a telescope for allowing visual observation within the cavity which includes an eye piece and an object lens which typically uses a fiber optic light source to illuminate the interior of the cavity. The object lens is located distal the eye piece. Another channel may be adapted to receive various instruments, such as suturing instruments or grasping devices or other suitable surgical devices. The channels are typically longitudinally located to provide axial arrangement of the telescope and instruments inside the tubular member. Such endoscopes also have a channel for allowing the passage of pressurized gas to expand the cavity of interest to an extent such that a visual image of the selected area can be seen on a display screen and/or seen by the operator through the eye piece connected to the optical telescope.

Consequently, intra-abdominal operations may be facilitated with only a small incision (approximately the size of the diameter of the laparoscope) which generally improves a patient's recovery time. Such devices may also have couplers for connection of laser devices to perform laser surgery.

Although such endoscopes help facilitate intracavity operations by providing a means for generating a visual image of the organ or tissue to be examined in conjunction with the necessary instrumentation for performing an operation on the object or tissue of interest, such devices are not typically suitable for intra-tissue operations or examinations since the object lens is generally unprotected and gets obstructed or covered with tissue debris, blood, or secretion when used to perform intra-tissue operations.

Typical endoscopic procedures that employ rigid endoscopes, generally require the use of a separate irrigation instrument which is inserted into the cavity of interest through an additional incision in the patient so that the area of operation may be washed. Such rigid intra-cavity devices do not have irrigation mechanisms for cleaning the visual observation device. For example, blood or other secretions may cover the object lens thereby negating the impact of visual observation, consequently the endoscope must be removed through a trocar sleeve for cleaning during the operating process. This slows down the operation process and increases the chances of infection since the instrument is removed and reinserted into the patient.

Flexible endoscopes are also known, such as gastroscopes and colonoscopes, which have irrigation channels within the instrument to spray the object lens to remove unwanted secretion or debris and thereby also avoid the necessity of making multiple incisions. However, such instruments are typically designed to be flexible so that they may be inserted through a winding and open channel such as an intestine. These devices are typically ineffective in penetrating solid tissue. As previously mentioned, such endoscope devices are also not suited to distend solid tissue.

Another problem with conventional intra-cavity medical instruments is the attachment method of a trocar sleeve to the patient. The endoscopes are typically inserted into a body cavity through an incision through the skin using a trocar and trocar sleeve as known in the art. A trocar sleeve typically has two opposing open ends to facilitate insertion of the laparoscope or other endoscope into the patient.

Several attachment methods are known for attaching a trocar sleeve at a certain position to the patient so that insertion and movement of the tubular member will not cause the trocar sleeve to move, thereby keeping a substantially airtight seal about the opening through which the tubular member is inserted into the patient. One such trocar, typically referred to as a Hasan trocar, uses a plastic or metallic member which is fixedly engageable with an exterior surface of the trocar sleeve so that a predetermined length of the trocar sleeve may be positioned inside the patient. The plastic or metallic member includes a conically shaped base portion or conical plug with circumferentially parallel ribs which are spaced apart so that the insertion of the base portion into the opening of the patient substantially forms an airtight seal between the trocar sleeve and the patient. The plug is typically inserted into the opening and below the skin line.

The member is fixedly secured to the patient by stitching a top portion of the plastic device, which remains outside the patient, to the outer skin tissue of the patient. The trocar sleeve may be slidably adjusted by loosening and tightening a laterally activating pinching mechanism which is located above the base portion. However, such attachment devices are time-consuming to attach given the two-step process of inserting the conical plug into the patient and subsequently stitching the exteriorly located top portion of the plastic device to the outer skin tissue of the patient.

Other known trocar devices rely solely on internally mounted plug devices to secure the trocar in place. One such known trocar sleeve attachment device includes a threaded base portion which is screwably twisted into the opening of the patient so as to secure the device in place to form an airtight seal between the trocar sleeve and the patient. As with the Hasan device, these devices are also slidably adjustable to the outside of the trocar sleeve via a laterally activated pinching device which may be tightened or loosened via a laterally fixed screw located above the threaded base portion. Another type of internally mounted attachment device similarly has a threaded base portion for screwably attaching to the patient, but instead of a lateral screw-tightening mechanism, uses an axially screw device.

However, such devices typically rely entirely on the threads to adequately engage the opening in the patient so as to provide a sufficient airtight seal. A problem arises given the elastic nature of the skin and subcutaneous fat tissues into which such devices are screwed, such devices typically do not provide adequate attachment when substantial movement of the endoscope is required.

Furthermore, different sized plug devices are required for different sized incisions since each plug has a predetermined size. For example, a small incision requires the use of a small diameter plug whereas a large incision requires a large diameter plug. Consequently, hospitals must maintain a sufficient size inventory of all sized devices. Also, a physician may make many different sized incisions during an operation and therefore require a plurality of different sized plug devices. Hence a need exists for a trocar attachment device which may be adjusted to seal various sized openings and also be adapted for external attachment to the patient to facilitate quick sealing and adjustment.

Consequently, there exists a need for a medical instrument which can be used to visually observe and simultaneously facilitate intra-tissue manipulation of a relatively solid tissue or organ. Such a device should also include a readily adjustable and easily attachable attachment mechanism for forming an airtight seal between the device and the opening in the patient so that movement of the device within the patient does not readily breach the airtight seal.

SUMMARY OF THE INVENTION

It is an object of the present invention to provide a medical instrument to facilitate intratissue dissection and/or suturing under direct vision by the operator of the medical instrument.

It is a further object of the present invention to provide an attachment mechanism which is readily adjustable and easily attachable to substantially seal the opening between the patient and the medical instrument.

It is a further object of the invention to provide a medical instrument having an image observation capability and irrigation system such that the irrigation system may clean the image observation mechanism to facilitate intra-tissue visual observation during suturing or observation.

Yet a further object of the invention is to provide a medical instrument having an outer sleeve member adapted to provide a small working area for an instrument which may be insertable through a channel in the medical device so as to expand distensible tissue to facilitate manipulation or dissection of the tissue while providing visual observation through an observation device wherein the observation device is not sufficiently obstructed by secretion or other visual obstruction.

The present invention includes a hollow sleeve member having a mechanism for distending tissue, such as a radially expandable penetration end, or other suitable end which is adapted for providing an open area within at least a portion of the distending mechanism, and an observation device which is movable into the distending mechanism, such as a telescope, for facilitating intra-tissue visual observation in the open area.

One embodiment includes an outer sleeve having a first end and a second end wherein the first end is the penetration end, such as a hollow cone adapted to expand and retract such that expansion of the penetration end moves tissue away from the first end. An inner sheath member adapted for insertion into the second end, includes channels for receiving the observation device and other instruments to manipulate or dissect tissue proximate the end of the device.

The penetration end may include a plurality of resilient wedge portions which form a substantially conically shaped end when the resilient wedge portions are retracted. Upon axial movement of the inner sheath, the wedge sections expand to form an open area in the end of the device. The inner sheath further includes an irrigation channel for spraying a liquid over the end of the observation device so as to clean an end of the observation device. The inner sheath also includes a suction channel for removing obstructions displaced by the irrigation action.

The device also includes a pronged device, such as a gripper, for securing the outer sleeve about the opening wherein the pronged grip device includes adjustable prongs which are axially slidable along the outer sleeve and radially contractible to form a substantially airtight seal between the outer sleeve and the opening.

A method for using the medical device includes inserting the device into the opening; adjusting the prong device, about the opening so as to substantially form an airtight seal between the outer sleeve and the opening; and moving the inner member and the outer member relative to each other to move tissue to provide an open area within the tissue. The method may further include the steps of applying gas pressure through the device to further distend the tissue and visually monitoring an area of interest inside the body through the visual observation device located inside the inner member when the distended mechanism forms the open area. The method may also include removing obstruction from the visual observation device by providing fluid flow over a portion of the visual observation device while the penetration end is inside the body.

BRIEF DESCRIPTION OF THE DRAWINGS

FIG. 13b is a front view of the distending mechanism of FIG. 13a.

DETAILED DESCRIPTION OF THE PREFERRED EMBODIMENTS

Figures 1, 2:
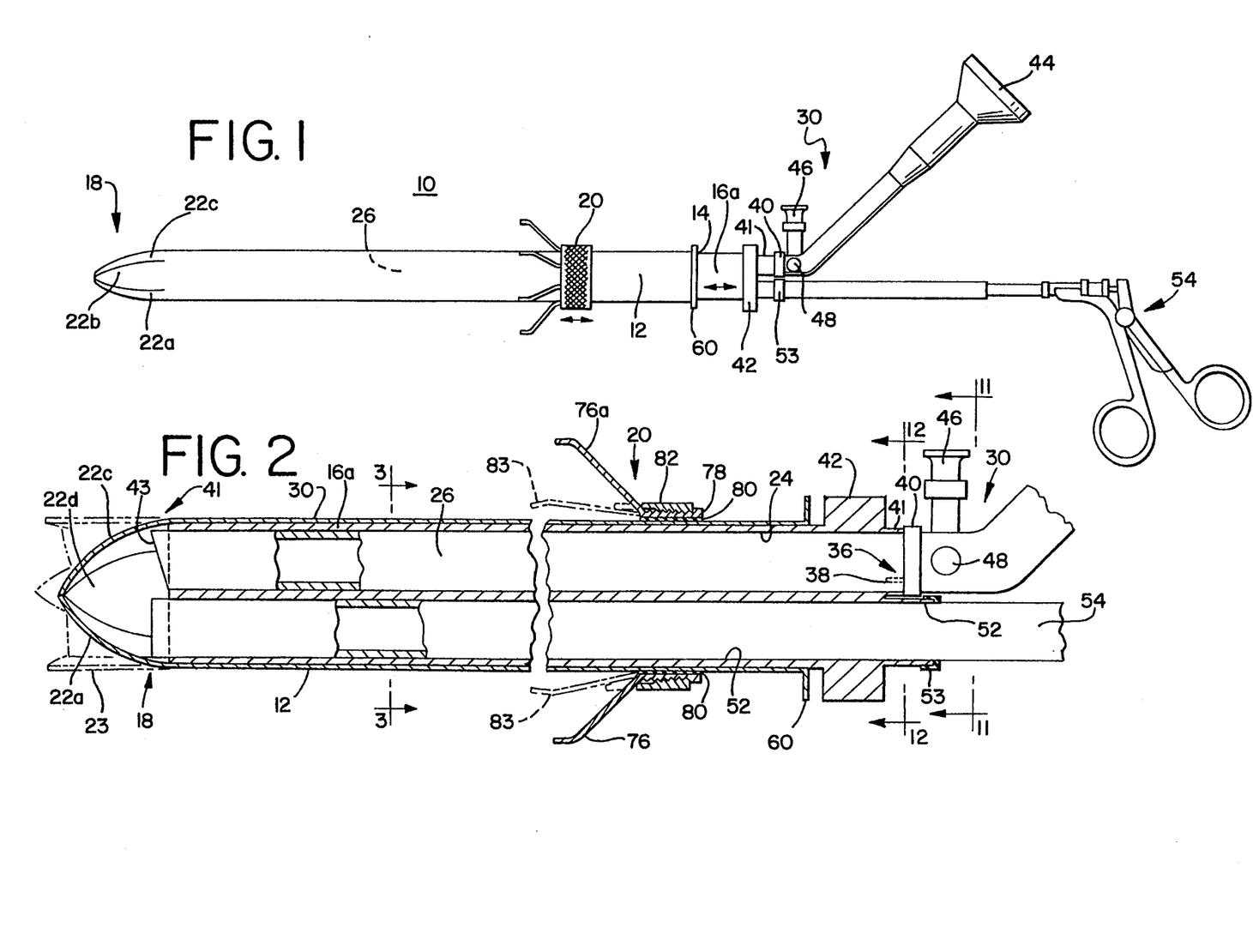
FIG. 1 is a side view of a medical device in accordance with the invention.
FIG. 2 is a partial cross-sectional view of the medical device shown in FIG. 1.
Figure 8:
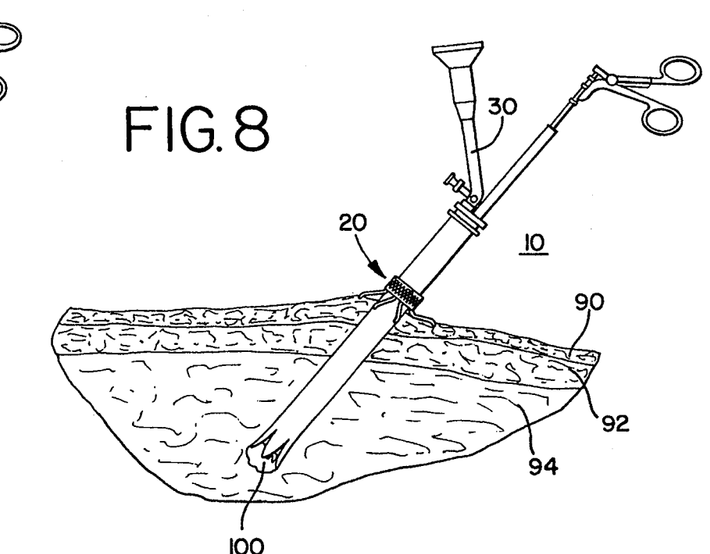
FIG. 8 illustrates the medical device attached to a patient and having the penetration end expanded within tissue to facilitate visual observation/manipulation of the tissue in accordance with the invention.

FIG. 1 depicts a medical device 10, referred to herein as a dissectoscope, which includes an outer tubular sleeve 12, having an open end 14 for receiving an inner sheath member 16a, a blunt penetration end 18 (or tissue distending mechanism) and an adjustable prong device 20 for attaching the outer sleeve 12 to outer skin tissue located about an incision or opening in the patient (best seen in FIG. 8). The outer tubular sleeve 12 may have a length of approximately 30 cm. The dissectoscope 10 may be inserted through an opening in a body to facilitate intra-tissue visual observation and/or manipulation of an area of interest within a solid tissue formation such as muscle tissue, a solid organ, or other tissue formation that does not have a cavity sufficient to allow use of an endoscope-type device.

The penetration end 18 includes a plurality of wedge sections 22a–22d or leaflets which form a blunt conical end when the wedges are not expanded. The wedge sections 22a–22d resiliently expand and retract radially outward and inward. Outward expansion is generally shown by dashed lines 23 in FIG. 2. The wedge sections 22a–22d serve to distend tissue away from the outer sleeve 12 so that the inner member 16a can be used to visually observe an area of interest at the end of the dissectoscope 10 and to facilitate use of additional instruments to perform dissections or other operations on the tissue as will be described later.

Figure 3:
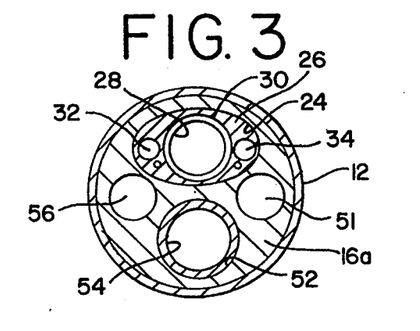
FIG. 3 is one embodiment of a cross-sectional view taken along line 3—3 in FIG. 2.

Referring to FIGS. 1–3, the inner sheath member 16a is adapted to slidably move inside the outer sleeve 12 and actuates the penetration end 18 as will be described later. The inner sheath member 16a includes an elliptical channel 24 (best seen in FIGS. 3–5) extending the axial length of the inner sheath 16a. The channel 24 is adapted to receive a visual observation device 26, such as one having an elliptical cross section. The visual observation device 26 includes a channel 28 adapted to receive an image viewing device, such as a telescope as known in the art, generally shown at 30. It will be recognized that any suitable image receiving device may also be used, such as an infra-red imaging device.

The visual observation device 26 also includes a fluid channel 32 for facilitating the flow of fluid out an angled end orifice 33 (best seen in FIG. 10) of the inner member 16a and a gas channel 34 for providing pressurized gas out another end orifice 35 of the inner member 16a. The angled end orifice 33 may be adapted to direct fluid toward the telescope so as to clean the end thereof. For example, the angled end orifice 33 may have inner walls forming an obtuse angle so as to direct fluid over the object lens of the telescope, or may be a metal hood affixed proximate to the end of the channel 32 so as to direct fluid over an object lens of the image viewing device 30.

The channels 32 and 34 are adapted to either directly or indirectly provide the gas or fluid to the end of the device 10. For example, a fluid may flow directly through the channel or indirectly where a tube containing fluid may be inserted through the fluid channel 32.

The visual observation device 26 also includes a locking mechanism 36 such as a protruding post 38 connected to a collar 40 and lockable in a detent 39 positioned in a collar 41 protruding from a shoulder 42. It will be recognized that any suitable locking device may also be used such as a rotatably actuated collar locking device as known in the art.

The image viewing device 30 includes an object lens 43 distal an eye lens 44. The object lens 43 as known in the art is angled at the distal end of the image transfer device 30 so as to provide adequate peripheral visual range.

The visual observation device 26 further includes an optical source connecting port 46, a gas connect port 48, and an irrigation port 50. As known in the art, the optical coupling port 46 connects to a light source (not shown) and provides illumination such that a user may visually see an area of interest through the object lens 43 located at the end of the telescope 30. The gas port 48 is connected to the gas channel 34 through a connecting inner passage (not shown) in the visual observation device 26 while the irrigation port 50 is connected to the irrigation channel 32 through another connecting passage (not shown).

A suction/irrigation channel 51 connects to a suction/irrigation device as known in the art (not shown), for removing unwanted secretions or other debris from proximate the end of the dissectoscope 10 and for spraying the operating area to remove unwanted obstructions. An instrument channel 52 is adapted to receive an operating instrument, such as a needle holder, or other operating instrument generally indicated at 54. Such devices may be approximately 5 mm in diameter. Therefore, the instrument channel 52 for receiving the instrument may also be slightly more than 5 mm so that there is sufficient clearance between the exterior surface of the instrument and the interior wall surface of the instrument channel 52 to allow the instrument to be inserted and slidably moved within the channel.

Another instrument channel 56 is adapted to receive an operating instrument such as a grasping forcep and may have a smaller diameter of approximately 3 mm to accommodate a smaller diameter instrument. Each of the entrance openings to the instrument channels 52 and 56 are covered with a rubber seal 53 and 57 respectively, as known in the art, having an opening in the center with a diameter less than that of the operating instrument to be inserted into the channel. The rubber seals 53 and 57 allow the operating instruments to freely slide within the channels and form a substantially air tight seal between the operating instruments and the surrounding air.

The eye lens 44 is positioned at approximately 135° with respect to the outer sleeve 12. Consequently, the light need only be reflected once to provide adequate visual images. This aspect is different from devices which require the light to be reflected over a plurality of 90° angles to transfer the light from the object lens to the eye piece 44. A loss of optical energy may result for each direction change. Therefore, the plurality of 90° reflective surfaces generally contribute to more loss of optical energy. The object lens angle is preferably about 30°. The cross-sectional diameter of the inner member 16a is approximately 14 to 16 mm. The thickness of the outer sleeve 12 may be approximately 1 mm.

The outer sleeve 12 has a shoulder 60 which prevents the pronged device 20 from sliding off the end of the outer sleeve 12, and also serves to provide an abutment surface with the shoulder 42 of the inner sheath member 16a. Therefore, the inner sheath member 16a may only travel a predetermined distance toward the penetration end 18.

Figure 4:
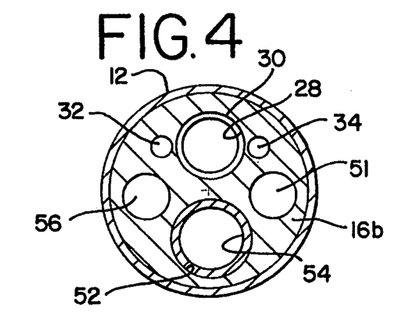
FIG. 4 is a cross-sectional view of an alternative embodiment showing separate channels in the inner member in accordance with the invention.

FIG. 4 depicts a cross-sectional view of an alternative embodiment of another inner member 16b and shows a plurality of separate channels for receiving the various devices previously described. In this embodiment, the visual observation device 26 is broken down into discrete components. For example, an elliptical channel in the inner member is not needed. A standard telescope with a circular cross section and collar may be inserted into channel 28 and lockingly connected to the inner member 16b using posts and detents or any other suitable locking device.

Figure 5:
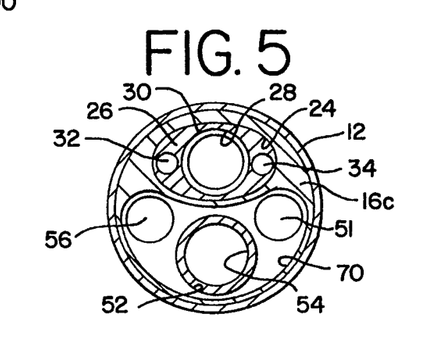
FIG. 5 is a cross-sectional view of another alternative embodiment showing a single channel in the inner sheath member for loosely housing a plurality of instruments in accordance with the invention.

FIG. 5 shows yet another embodiment depicting an inner sheath member 16c having a cross section with two channels. A first channel is similar to channel 24 of FIG. 3, wherein an elliptical visual observation device may be inserted. A second larger channel 70 does not have separate channels for the operating instruments and a suction/irrigation mechanism as shown in FIGS. 3 and 4. This embodiment offers flexibility and greater ability to move the operating instruments over a larger area within the inner member.

Referring back to FIGS. 2 and 3, the irrigation channel 32 serves as a cleaning mechanism for spraying the object lens 43 when the object lens becomes smeared or otherwise obstructed with pieces of cut tissue, bodily secretions, or other fluids. A hood 72 (best seen in FIG. 10), attached via a rivet, glue or other suitable attachment mechanism, extends beyond the end surface of the inner member and is angled so that fluid through the irrigation channel is sufficiently directed over the angled object lens 43. The gas channel 34 may then be used to remove any obstructions displaced by the irrigation mechanism. Consequently, the cleaning mechanism includes an irrigation device and subsequent suction mechanism to ensure adequate cleaning of the object lens 43 while the observation is within a solid tissue formation.

The penetration end 18 is formed from the plurality of resilient wedge sections or leaflets such that the natural state of the penetration end 18 provides a blunt tip for the dissectoscope 10. The wedge sections 22a-22d are radially expanded when the inner sheath member 16a moves axially forward such that an exterior surface of the inner member 16a engages an interior surface of the wedge sections 22a through 22d, thereby forcing the wedges outward. Consequently, any tissue which was abutting the exterior surface of the penetration end 18 is now moved away from the inner sheath member 16a.

Figure 6:
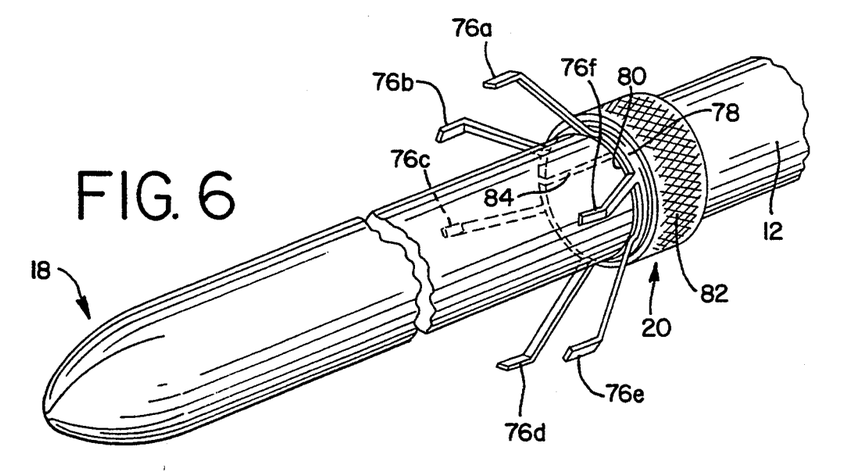
FIG. 6 is a sectional perspective view of the medical device in accordance with the invention showing an attachment device for forming an airtight closure with the outer sleeve member.

FIG. 6 depicts the penetration end 18 in a closed or completely retracted state and the attachment device 20 in an unretracted state. The attachment device 20 includes a plurality of prongs 76a-76f which are connected to a slotted threaded member 78 which is adapted for axial movement along the exterior surface of the outer sleeve 12. The inner surface of the prong device 20 has a layer of rubber 80 which helps prevent slippage and affords a tighter grip when the prong device is tightened to the outer sleeve 12. The slotted threaded member 78 has an outer screwably engaging member 82, which when threadably adjusted clockwise, moves toward the penetration end 18 of the dissectoscope 10, and causes the prongs 76a-76f to be forced toward the outer sleeve 12 (shown as dashed lines 83 in FIG. 2) and also reduces a slot area 84 which causes clamping of the slotted threaded member 78 around the outer sleeve 12. Conversely, when the outer screwably engaging member 82 is rotated counterclockwise, the engaging member 82 retracts toward the open end of the outer sleeve 12 causing the prongs 76a-76f to move away from the outer sleeve 12 and loosens the slotted threaded member 78 about the outer sleeve 12.

Figure 7:
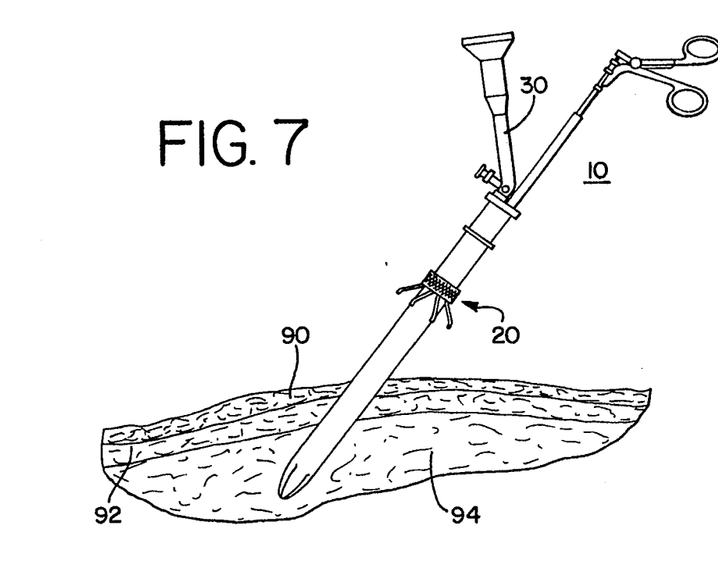
FIG. 7 illustrates the insertion of the medical device through a plurality of solid tissue formations using a closed penetration end in accordance with the invention.

FIGS. 7 and 8 generally depict the dissectoscope 10 being inserted through several tissue layers 90 and 92 and into a solid tissue of interest which is to be visually observed and/or dissected. For example, the first layer 90 may be skin, the second layer 92 may be fat, and the tissue area of interest 94 may be a tumor, muscle, or herniated organ. To use the dissectoscope 10, an incision is made into the skin sufficient to allow the outer sleeve 12 to be inserted through the opening caused by the incision. The operator inserts the dissectoscope 10 into the patient.

The operator then pushes the dissectoscope 10 into and through the various tissue layers which may be readily accomplished due to the conical shape of the penetration end 18. To determine the location of the dissectoscope, the operator moves the inner member 16a relative to the outer member 12 to engage the wedge sections so as to radially expand the wedge sections. The opening of the wedge sections causes distending of the tissue surrounding the outer surface of the wedge sections (best seen in FIG. 8). With the object lens still inside the inner member, a pocket or void is produced directly in front of the object lens. This may allow enough space to obtain a visual image of the area in front of the penetration end and the operator may use the scope to visually observe the area of tissue that is directly in front of the dissectoscope.

Also, the operator may cause gas to be projected through the gas channel 34 to further distend the tissue (best seen in FIGS. 8 and 9) so as to provide a larger open area proximate the end of the device. The operator may then decrease the flow of gas and retract the inner sheath 16a to cause the wedge sections to resiliently retract and then may continue to insert the dissectoscope further into the tissue.

The process of boring or penetrating further into the tissue and periodically monitoring the area in front of the dissectoscope may be repeated until the operator reaches the tissue area of interest. Once the area of destination has been reached, the prong device 20 may be actuated so that the prongs clamp into the external skin tissue of the patient about the opening to form a substantially airtight seal between the outer sleeve 12 of the dissectoscope 10 and the opening in the patient.

The penetration end may be used to distend tissue as previously described to facilitate visual observation of the area of interest. Dissection or manipulation of the tissue may then begin by visually monitoring the area of interest through the scope located inside the inner member when the wedge sections are expanded. When the object lens is obstructed, the obstruction may be removed by providing fluid flow over a portion of the object lens and subsequently using the suction channel to draw out the debris or excess fluid that caused the obstruction.

Figure 9:
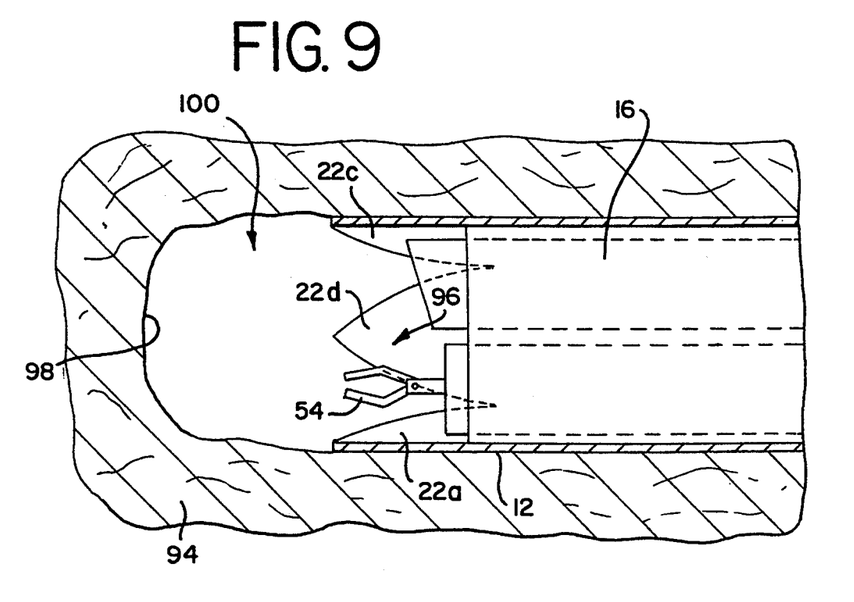
FIG. 9 generally depicts the penetration end forming an open area to facilitate intra-tissue observation/manipulation within a tissue formation of interest in accordance with the invention.

FIG. 9 illustrates the penetration end of the dissectoscope 10 inserted into the tissue formation 94 with the wedge sections 22a–22d completely extended. The wedge sections 22a–22d distend the tissue outwardly to provide an open area 96 within at least a portion of the outer sleeve member 12. The open area 96 remains substantially free of tissue due to the wall-like effect of the wedge sections. An extended open area 100 may be formed by pressure caused by gas insufflation through the gas channel 34. The open areas 96 and 100 facilitate observation and/or manipulation of tissue located outside of the open area 98. Since the penetration end extends beyond the end of the observation device and the operating instrument, the open area 96 provides enough free space to allow an optical telescope to function and to provide room for manipulation of the instrument. Hence the telescope can be used for intra-tissue visual observation in the open areas 96 and 100.

Although not illustrated, the device may find particular use in expanding layers of tissue. For example, the device may be inserted between layers of tissue whereafter the wedge portions and gas pressure may be used to slightly expand the area between the layers to facilitate observation and/or manipulation (e.g. removal of a polyp or cyst in a breast) of the tissue of interest.

Figure 10:
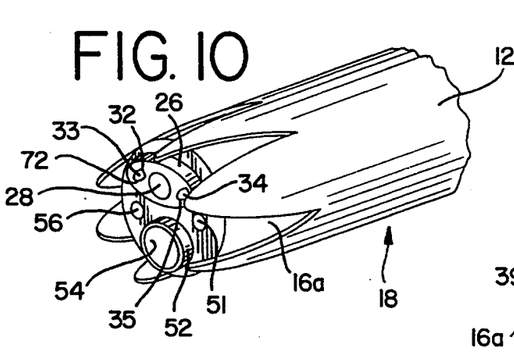
FIG. 10 is a partial perspective view of the inner sheath member engaging the penetration end in accordance with the invention.

FIG. 10 generally depicts the inner sheath member 16a actuating the wedge sections. The operating instrument 54 (forceps not shown) may be moved to extend past the end of the inner sheath member 16a to facilitate suturing or other activity.

Figure 11:
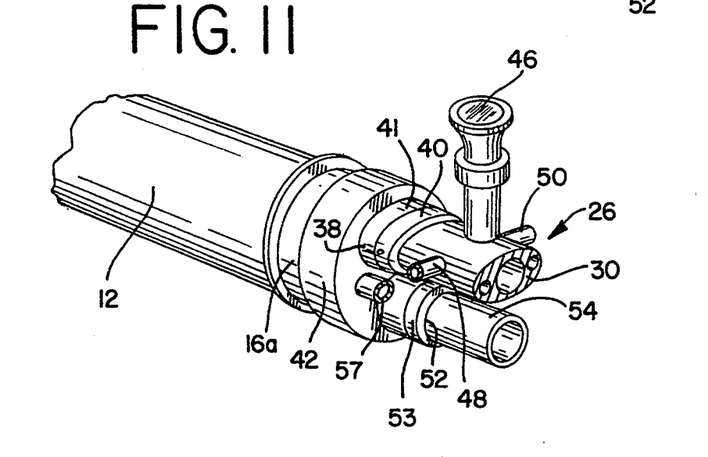
FIG. 11 is a partial perspective view of the inventive medical device shown at lines 11—11 in FIG. 2.
Figure 12:
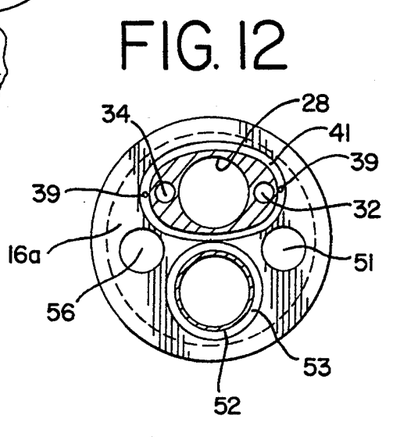
FIG. 12 is a cross-sectional view of the medical device taken along lines 12—12 of FIG. 2.

FIGS. 11 and 12 generally show the elliptical observation device 30 connected at the collar 40. The various connection ports 46, 48 and 50 are also shown.

Figure 13A:
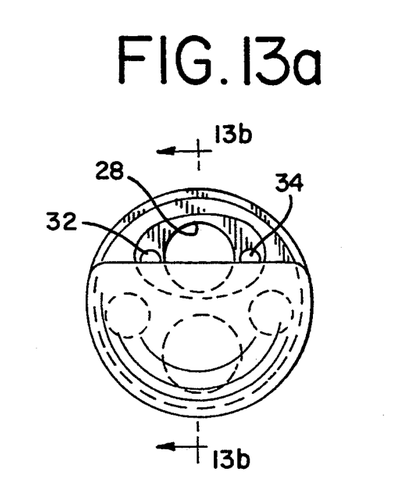
FIG. 13a is a cross-sectional view of an alternative embodiment of a distending mechanism in accordance with the invention.
Figure 13B:
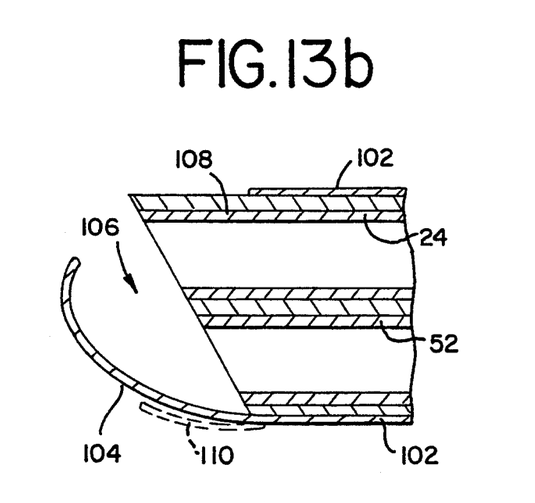

FIGS. 13a–13b illustrate another embodiment of the invention wherein the outer sleeve does not have a plurality of wedges portions and the end surface of the inner sheath is not substantially flat. The outer sleeve 102 has a curved penetration end 104 extending in front of an oblique end 106 of the inner sheath 108 to cover at least a portion of the end of the inner sheath 108. To distend tissue and facilitate observation and manipulation of tissue, the hollow outer sleeve 102 is retracted or the inner sheath is advanced thereby causing the curved penetration end 104 to flex away from the oblique end 106 and slide under the oblique end as indicated by dashed lines 110.

It will be recognized that the outer sleeve 12 and inner sheath may be made from metal, plastic or any other suitable material. The material for the outer sleeve 12 should have resilient qualities sufficient to provide expansion and retraction of the wedge sections. The prong device 20 may also be made from metal or other suitable flexible material.

In an alternative embodiment, the dissectoscope may have an inner member with a more conically shaped end to provide penetration action. The sheath may be a cylinder which may slidably extend beyond the end of the inner member to distend tissue away from the end instead of the leaflets. In such an embodiment, no expandable or retractable sections are needed.

In another alternative embodiment, the penetration end 18 may be a separate removable piece with threads for screwably engaging a threaded end of the sleeve member 12 so that a number of different styled penetration ends may be used with one type of sleeve member. For example, one style of penetration end may have four wedge sections whereas another style may only have two wedge sections. The bluntness of the penetration end may also vary depending upon the application.

In yet another embodiment, the penetration end may be in the form of a pivotal cover over the end of the sheath member which may be opened and closed using a push or pull mechanism.

Specific embodiments of novel apparatus and methods for facilitating intra-tissue visual observation and/or manipulation of distensible tissue have been described for the purposes of illustrating the manner in which the invention may be used and made. It should be understood that the implementation of other variations and modifications of the invention will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. A medical device for insertion into body tissue comprising:
   an outer sleeve member;
   penetration means disposed at a first end of said sleeve member for facilitating entry of said sleeve into the body tissue and effecting intra-tissue distension to provide an open area within the tissue in communication with said first end; and
   observation means operatively coupled with said penetration means for facilitating intra-tissue visual observation through said first end of said sleeve member and of said open area.

2. The device of claim 1 wherein said intra-tissue distention includes distending tissue such that said tissue is forced away from said first end to allow said open area to be substantially free of tissue such that said open area facilitates observation and/or manipulation of tissue located about said open area.

3. The device of claim 2 further comprising means, movable through said sleeve member, for manipulating the tissue located outside said open area.

4. The device of claim 2 further comprising means, operatively coupled to said sleeve member, for providing a substantially airtight seal between said sleeve member and the opening.

5. The device of claim 4 wherein said airtight sealing means comprises prong means, slidably adjustable about an exterior surface of said sleeve member.

6. The device of claim 1 further comprising pressure medium facilitating means for allowing a medium under pressure to be directed into said open area to provide intra-spacial pressure in said open area.

7. The medical device of claim 1 wherein said observation means is axially engageable with said penetration means for distending tissue such that axial movement of said observation means relative to said sleeve member facilitates either the radial expansion or retraction of said penetration means for distending tissue.

8. The medical device of claim 1 wherein said penetration means for distending comprises a plurality of resilient wedge portions which form a substantially conically shaped end of said sleeve member when the resilient wedge portions are retracted.

9. The medical device of claim 1 further comprising an image receiving device for lockingly engaging in said observation means to substantially prevent axial movement of said image receiving device within said observation means.

10. The medical device of claim 1 wherein said observation means includes means for visually observing an area proximate said first end, and
    an inner member extending within said outer sleeve and including a channel for receiving said visual observation means.

11. The medical device of claim 10 wherein said visual observation means includes an image receiving device, and
    means for cleaning an object lens of said image receiving device with liquid, said object lens being disposed generally proximate said penetration means.

12. The medical device of claim 11 wherein said cleaning means includes a channel formed by said visual observation means for transporting the liquid, and
    a means disposed generally adjacent said object lens for directing the liquid over said object lens.

13. The medical device of claim 11 wherein said visual observation means further includes means for facilitating suction for removing obstructions displaced by said cleaning means.

14. The medical device of claim 10 wherein said inner member forms,
    a first channel for providing compressed gas or suction to or from an end of said member proximate said penetration means,
    a second channel for receiving said visual observation means, and
    a third channel adapted to receive at least one instrument to facilitate manipulation of tissue located about said penetration means.

15. The medical device of claim 14 wherein said inner member further forms a fourth channel adapted to receive at least one instrument to facilitate manipulation of tissue located about said penetration means.

16. The medical device of claim 15 wherein said third and fourth channels are generally tubular and said third channel has a diameter less than said fourth channel.

17. The medical device of claim 10 wherein said inner member forms a channel to allow at least one instrument to extend through said outer sleeve and manipulate tissue located about said penetration means.

18. The medical device of claim 1 wherein said observation means also forms a means for allowing at least one instrument to be inserted into a second end of said sleeve and extended through said first end to manipulate tissue located about said penetration means.

19. A medical device for insertion into an opening in a body comprising:
    an outer sleeve member;
    penetration means disposed at a first end of said sleeve member for facilitating entry of said sleeve into the body tissue and effecting intra-tissue distention to provide an open area within the tissue in communication with the open end; and
    observation means extending through said sleeve for intratissue visual observation through said first end of said sleeve member and of said open area, said observation means including an inner member forming,
    a first channel for providing compressed gas or suction to or from an end of said member proximate said penetration means,
    a second channel for receiving a means for visually observing an area proximate said end of said member, and
    a third channel adapted to allow at least one instrument to extend through said first end to manipulate tissue located about said penetration means.

* * * * *